US012661141B2

(12) United States Patent
Cowley et al.

(10) Patent No.: US 12,661,141 B2
(45) Date of Patent: Jun. 23, 2026

(54) ARTICULATING ULTRASONIC SURGICAL INSTRUMENTS AND SYSTEMS

(71) Applicant: Covidien LP, Mansfield, MA (US)

(72) Inventors: Matthew S. Cowley, Frederick, CO (US); Thomas E. Drochner, Longmont, CO (US); Michael B. Lyons, Boulder, CO (US); David J. Van Tol, Boulder, CO (US); James R. Fagan, Erie, CO (US)

(73) Assignee: Covidien LP, Mansfield, MA (US)

( * ) Notice: Subject to any disclaimer, the term of this patent is extended or adjusted under 35 U.S.C. 154(b) by 412 days.

(21) Appl. No.: 17/924,206

(22) PCT Filed: May 24, 2021

(86) PCT No.: PCT/US2021/033807
§ 371 (c)(1),
(2) Date: Nov. 9, 2022

(87) PCT Pub. No.: WO2021/242656
PCT Pub. Date: Dec. 2, 2021

(65) Prior Publication Data
US 2023/0240702 A1     Aug. 3, 2023

Related U.S. Application Data

(60) Provisional application No. 63/030,057, filed on May 26, 2020.

(51) Int. Cl.
*A61B 17/32* (2006.01)
*A61B 17/00* (2006.01)
(Continued)

(52) U.S. Cl.
CPC ................. *A61B 17/320092* (2013.01); *A61B 2017/00738* (2013.01); *A61B 2017/2825* (2013.01);
(Continued)

(58) Field of Classification Search
CPC .. A61B 17/320092; A61B 2017/00738; A61B 2017/2825; A61B 2017/320074;
(Continued)

(56) References Cited

U.S. PATENT DOCUMENTS

| | | | |
|---|---|---|---|
| 5,792,135 A | 8/1998 | Madhani et al. | |
| 5,897,523 A | 4/1999 | Wright et al. | |

(Continued)

FOREIGN PATENT DOCUMENTS

| | | |
|---|---|---|
| WO | 2016/085753 A1 | 6/2016 |
| WO | 2020198372 A1 | 10/2020 |

(Continued)

OTHER PUBLICATIONS

U.S. Appl. No. 17/734,146, filed May 2, 2022, Inventor: Michael B. Lyons.

(Continued)

*Primary Examiner* — Todd J Scherbel

(57) ABSTRACT

An ultrasonic end effector includes a substantially cylindrical blade and a jaw including a structural body and a jaw liner. The jaw is movable from an open to a clamping position, wherein the blade-facing surface of the jaw liner opposes the blade with the first and second blade-facing surfaces of the structural body disposed on either side of the jaw liner and the blade. The blade defines a first longitudinal axis and a first radius, the first and second blade-facing surfaces of the structural body cooperate to define a second radius centered on a second longitudinal axis, and the blade-facing surface of the jaw liner defines a third radius (Continued)

centered on a third longitudinal axis. The first radius and the second radius of curvature are different from one another.

9 Claims, 6 Drawing Sheets

(51) Int. Cl.
    *A61B 17/28*         (2006.01)
    *A61B 90/00*         (2016.01)

(52) U.S. Cl.
    CPC ............. *A61B 2017/320074* (2017.08); *A61B 2017/320094* (2017.08); *A61B 2090/035* (2016.02)

(58) Field of Classification Search
    CPC .. A61B 2017/320094; A61B 2090/035; A61B 2017/320072; A61B 2017/320093; A61B 2017/320095; A61B 2090/034; A61B 18/1445; A61B 18/1442
    See application file for complete search history.

(56) References Cited

U.S. PATENT DOCUMENTS

| | | | |
|---|---|---|---|
| 7,135,030 | B2 | 11/2006 | Schwemberger et al. |
| 10,172,636 | B2 | 1/2019 | Stulen et al. |
| 10,226,274 | B2 | 3/2019 | Worrell et al. |
| 10,258,363 | B2 | 4/2019 | Worrell et al. |
| 10,335,182 | B2 | 7/2019 | Stulen et al. |
| 10,405,876 | B2 | 9/2019 | Boudreaux |
| 10,413,316 | B2 | 9/2019 | Lyons |
| 10,492,819 | B2 | 12/2019 | Hibner |
| 10,575,836 | B2 | 3/2020 | Hibner et al. |
| 10,912,581 | B2 | 2/2021 | Stulen et al. |
| 10,925,630 | B2 | 2/2021 | Cuti et al. |
| 10,987,123 | B2 | 4/2021 | Weir et al. |
| 11,337,717 | B2 | 5/2022 | Lyons |
| 2006/0058825 | A1 | 3/2006 | Ogura et al. |
| 2006/0190034 | A1 | 8/2006 | Nishizawa et al. |
| 2008/0214967 | A1 | 9/2008 | Aranyi et al. |
| 2009/0163948 | A1 | 6/2009 | Sunaoshi et al. |
| 2012/0253370 | A1 | 10/2012 | Ross et al. |
| 2013/0012959 | A1 | 1/2013 | Jinno |
| 2013/0140835 | A1 | 6/2013 | Stefanchik |
| 2014/0005701 | A1 | 1/2014 | Olson et al. |
| 2014/0005702 | A1* | 1/2014 | Timm .................... A61B 17/29 606/169 |
| 2014/0012298 | A1* | 1/2014 | Cunningham . A61B 17/320092 606/169 |
| 2014/0276931 | A1 | 9/2014 | Parihar et al. |
| 2014/0309562 | A1 | 10/2014 | Ito |
| 2014/0350570 | A1 | 11/2014 | Lee |
| 2015/0080924 | A1 | 3/2015 | Stulen et al. |
| 2015/0148831 | A1 | 5/2015 | Faller et al. |
| 2015/0157354 | A1* | 6/2015 | Bales, Jr. .............. B06B 1/0223 606/169 |
| 2015/0164538 | A1 | 6/2015 | Aldridge et al. |
| 2016/0302812 | A1 | 10/2016 | Monroe et al. |
| 2017/0105752 | A1* | 4/2017 | Boudreaux ........ A61B 17/3203 |
| 2017/0164997 | A1* | 6/2017 | Johnson ............. A61B 18/1445 |
| 2017/0202607 | A1* | 7/2017 | Shelton, IV ............. A61N 7/02 |
| 2017/0238959 | A1* | 8/2017 | Craig ............. A61B 17/320092 |
| 2018/0132887 | A1* | 5/2018 | Asher ........... A61B 17/320092 |
| 2019/0000499 | A1 | 1/2019 | Stokes et al. |
| 2019/0021752 | A1 | 1/2019 | Boudreaux |
| 2019/0021756 | A1 | 1/2019 | Boudreaux |
| 2019/0133635 | A1 | 5/2019 | Stulen et al. |
| 2019/0216491 | A1 | 7/2019 | Meiser et al. |
| 2019/0216493 | A1 | 7/2019 | Worrell et al. |
| 2019/0216530 | A1 | 7/2019 | Kabala et al. |
| 2019/0231385 | A1 | 8/2019 | Cowley |
| 2019/0247083 | A1 | 8/2019 | Worrell et al. |
| 2019/0290318 | A1 | 9/2019 | Boudreaux |
| 2019/0321068 | A1 | 10/2019 | Hibner et al. |
| 2019/0321069 | A1 | 10/2019 | Hibner |
| 2019/0321070 | A1 | 10/2019 | Boudreaux |
| 2019/0380735 | A1 | 12/2019 | Cuti et al. |
| 2020/0229833 | A1 | 7/2020 | Vakharia et al. |
| 2020/0229834 | A1 | 7/2020 | Olson et al. |
| 2020/0237397 | A1 | 7/2020 | Boudreaux |
| 2020/0237399 | A1 | 7/2020 | Stulen et al. |
| 2021/0353324 | A1 | 11/2021 | Fagan et al. |
| 2021/0353325 | A1 | 11/2021 | Fagan et al. |
| 2021/0369295 | A1 | 12/2021 | Cowley |

FOREIGN PATENT DOCUMENTS

| | | |
|---|---|---|
| WO | 2021006984 A1 | 1/2021 |
| WO | 2021173294 A1 | 9/2021 |
| WO | 2021178103 A1 | 9/2021 |
| WO | 2021202035 A1 | 10/2021 |

OTHER PUBLICATIONS

U.S. Appl. No. 17/798,273, filed Aug. 8, 2022, Inventor: James R. Fagan.

U.S. Appl. No. 17/970,257, filed Oct. 20, 2022, Inventor: Matthew S. Cowley.

International Search Report and Written Opinion received for PCT Patent Application No. PCT/US2021/033807, mailed on Sep. 21, 2021, 21 pages.

Invitation to Pay Addition Fees and Partial International Search Report received for PCT Patent Application No. PCT/US2021/033807, mailed on Jul. 29, 2021, 11 pages.

Chinese Office Action for corresponding CN Application No. 202180038024.4 mailed Jan. 25, 2026 (11 pages), English translation of first page.

* cited by examiner

280

284

2851

2852

282

286

280

286

284

282

2851

2852

ARTICULATING ULTRASONIC SURGICAL INSTRUMENTS AND SYSTEMS

CROSS-REFERENCE TO RELATED APPLICATION

This application is a § 371 National Stage Application of International Patent Application No. PCT/US2021/033807, filed on May 24, 2021, which claims the benefit of, and priority to, U.S. Provisional Patent Application No. 63/030, 057, filed on May 26, 2020, the entire contents of each of which is hereby incorporated herein by reference.

FIELD

The present disclosure relates to surgical instruments and systems and, more particularly, to articulating ultrasonic surgical instruments and systems.

BACKGROUND

Ultrasonic surgical instruments and systems utilize ultrasonic energy, i.e., ultrasonic vibrations, to treat tissue. More specifically, a typical ultrasonic surgical instrument or system includes a transducer configured to produce mechanical vibration energy at ultrasonic frequencies that is transmitted along a waveguide to an ultrasonic end effector configured to treat, e.g., coagulate, cauterize, fuse, seal, cut, desiccate, or otherwise treat, tissue.

Some ultrasonic surgical instruments and systems incorporate rotation features, thus enabling rotation of the ultrasonic end effector to a desired orientation within the surgical site. However, even in such instruments and systems, the ability to navigate within the surgical site via rotation and manipulation alone is limited.

SUMMARY

As used herein, the term "distal" refers to the portion that is being described which is closer to a patient (and, thus, farther from the surgeon, robot, or other operator), while the term "proximal" refers to the portion that is being described which is farther from the patient (and, thus, closer to the surgeon, robot, or other operator). Further, to the extent consistent, any or all of the aspects detailed herein may be used in conjunction with any or all of the other aspects detailed herein.

Provided in accordance with the present disclosure is an end effector of an ultrasonic surgical instrument including an ultrasonic blade having a substantially cylindrical configuration and a jaw including a structural body and a jaw liner engaged with the structural body. The jaw liner is positioned such that a blade-facing surface of the jaw liner is disposed between first and second blade-facing surfaces of the structural body. The jaw is movable relative to the ultrasonic blade from an open position to a clamping position, wherein, in the clamping position, the blade-facing surface of the jaw liner opposes the ultrasonic blade with the first and second blade-facing surfaces of the structural body disposed on either side of the blade-facing surface of the jaw liner and the ultrasonic blade. The ultrasonic blade, the first and second blade-facing surfaces of the structural body, and the blade-facing surface of the jaw liner, define first, second, and third longitudinal axes, respectively, that are substantially parallel or coaxial with one another when the jaw is disposed in the clamping position. The ultrasonic blade defines a first radius centered on the first longitudinal axis, the first and second blade-facing surfaces of the structural body cooperate to define a second radius centered on the second longitudinal axis, and the blade-facing surface of the jaw liner defines a third radius centered on the third longitudinal axis. Two or more of the radii may be different from one another and/or two or more of the radii may be equal to one another. In the clamping position of the jaw, the first and third longitudinal axes may be offset relative to one another. Additionally or alternatively, in aspects, the first and second blade-facing surfaces of the structural body or the blade-facing surface of the jaw liner may be non-arcuate, e.g., planar, multi-angled, multi-curved, etc.

In an aspect of the present disclosure, two or more of the longitudinal axes are parallel and offset relative to one another in the clamping position of the jaw. In such aspects, for example, the first longitudinal axis may be offset farther towards the jaw as compared to the second and/or third longitudinal axes in the clamping position of the jaw.

In another aspect of the present disclosure, at least two of the three radii are substantially equal and/or at least two of the longitudinal axes are substantially coaxial with one another in the clamping position of the jaw.

In still another aspect of the present disclosure, in the clamping position of the jaw, the blade-facing surface of the jaw liner protrudes beyond the first and second blade-facing surfaces of the structural body within a width of the ultrasonic blade. In such aspects, in the clamping position of the jaw, at least a portion of each of the first and second blade-facing surfaces of the structural body may protrude beyond the blade-facing surface of the jaw liner outside a width of the ultrasonic blade. Alternatively, the first and second blade-facing surfaces of the structural body may be disposed within or extend to a width of the ultrasonic blade. Further, the structural body may not protrude beyond the jaw liner within or outside of the width of the ultrasonic blade, may protrude beyond the jaw liner both within and outside the width of the blade, or may protrude beyond the jaw liner within the width of the blade but not outside the width of the blade.

In yet another aspect of the present disclosure, the jaw is rotatable about the ultrasonic blade to a plurality of different orientations such that the jaw is movable to the clamped position in each of the plurality of different orientations to oppose the blade-facing surface of the jaw liner with a plurality of different surface portions of the ultrasonic blade.

In still yet another aspect of the present disclosure, the end effector includes a distal housing with the structural body of the jaw pivotably coupled to the distal housing and the ultrasonic blade extending distally from the distal housing. In such aspects, a plug may be disposed within the distal housing surrounding the ultrasonic blade to inhibit passage of material proximally into the distal housing and/or an ultrasonic transducer may be disposed within the distal housing and operably coupled to the ultrasonic blade.

Another end effector of an ultrasonic surgical instrument includes a distal housing, an ultrasonic blade extending distally from the distal housing, and a jaw including a structural body pivotably coupled to the distal housing and a jaw liner engaged with the structural body between first and second outer side edges of the structural body. The jaw is pivotable relative to the ultrasonic blade from an open position to a clamping position, wherein the blade-facing surface of the jaw liner opposes the ultrasonic blade with the first and second outer side edges of the structural body disposed on either side of the jaw liner and the ultrasonic blade. The distal housing includes an extension portion surrounding a portion of the ultrasonic blade and including uprights disposed on either side of the ultrasonic blade. The uprights define shelves at the free ends thereof configured to act as stops to inhibit further pivoting of the jaw towards the ultrasonic blade upon contact of the first and second outer side edges of the structural body with the shelves.

In an aspect of the present disclosure, the shelves act as the stops in a worn condition of the jaw liner and wherein, in an unworn condition of the jaw liner, the jaw liner is configured to contact the ultrasonic blade prior to contact of the first and second outer side edges of the structural body with the shelves upon pivoting of the jaw towards the ultrasonic blade such that a gap is maintained between the first and second outer side edges of the structural body and the shelves in the clamping position of the jaw.

In another aspect of the present disclosure, the extension portion defines a U-shaped configuration including a back-span interconnecting the uprights.

In yet another aspect of the present disclosure, the shelves extend substantially perpendicularly relative to the uprights.

In still another aspect of the present disclosure, the extension portion extends along less than about 20% of a length of an operative portion of the ultrasonic blade. Alternatively, the extension portion may extend along at least about 80% of a length of an operative portion of the ultrasonic blade.

In still yet another aspect of the present disclosure, a plug is be disposed within the distal housing surrounding the ultrasonic blade to inhibit passage of material proximally into the distal housing and/or an ultrasonic transducer is be disposed within the distal housing and operably coupled to the ultrasonic blade.

In another aspect of the present disclosure, the distal housing and the jaw are rotatable about the ultrasonic blade to position the jaw in a plurality of different orientations about the ultrasonic blade. The jaw is movable, in such aspects, to the clamped position in each of the plurality of different orientations to oppose the jaw liner with a plurality of different surface portions of the ultrasonic blade.

In another aspect of the present disclosure, the ultrasonic blade defines a substantially cylindrical configuration having a radius centered on a longitudinal axis and the blade-facing surface of the jaw liner has a radius of curvature substantially equal to the radius and substantially centered on the longitudinal axis.

In yet another aspect of the present disclosure, the structural body of the jaw includes a distal end portion having at least one of a chamfered outer surface or undercut inner surfaces.

The details of one or more aspects of the disclosure are set forth in the accompanying drawings and the description below. Other features, objects, and advantages of the instruments and techniques described in this disclosure will be apparent from the description and drawings, and from the claims.

DETAILED DESCRIPTION

Figure 1A:
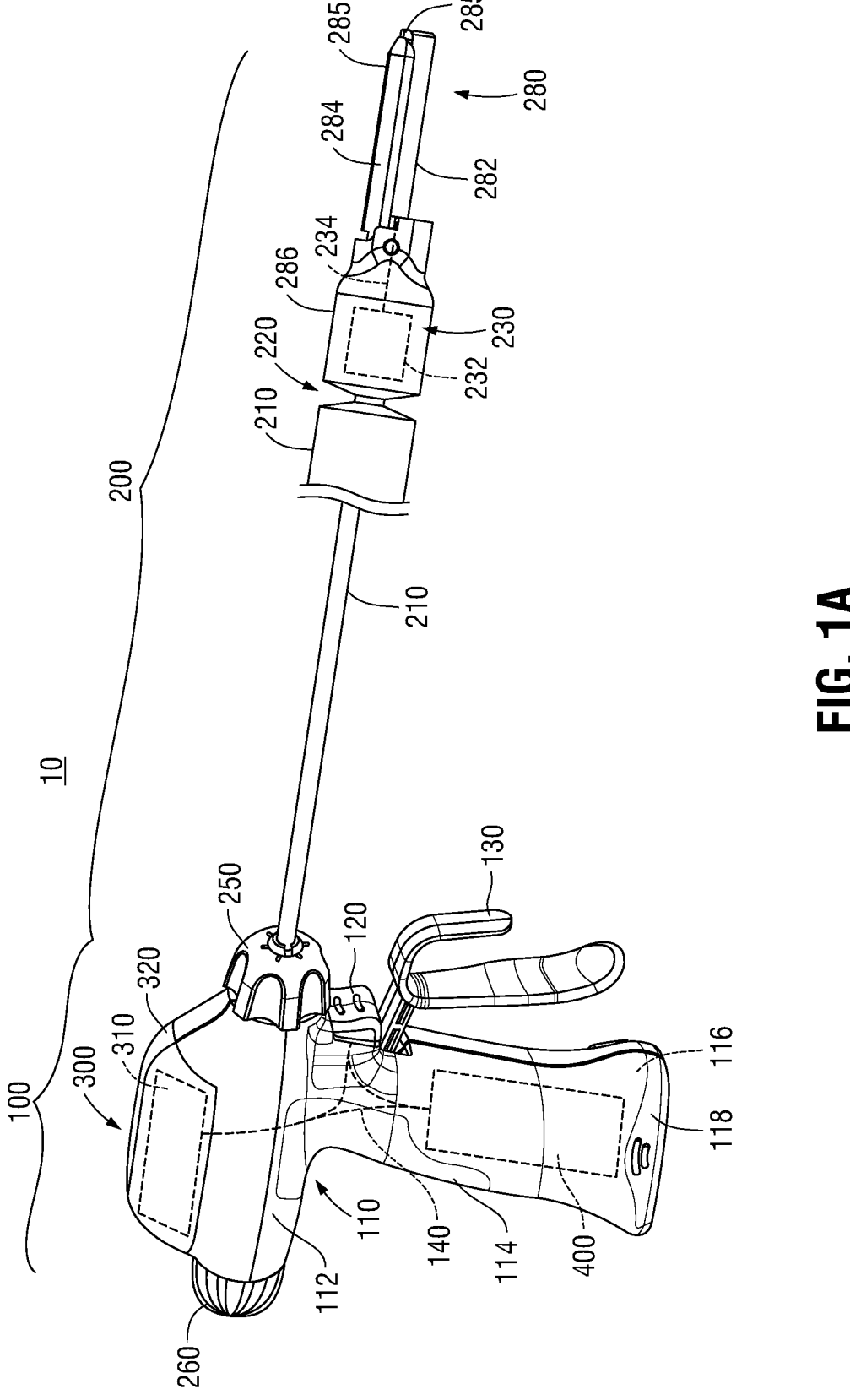
FIG. 1A is a perspective view of a hand-held articulating ultrasonic surgical instrument provided in accordance with the present disclosure with a distal portion thereof enlarged, disposed in an un-articulated position.
Figure 1B:
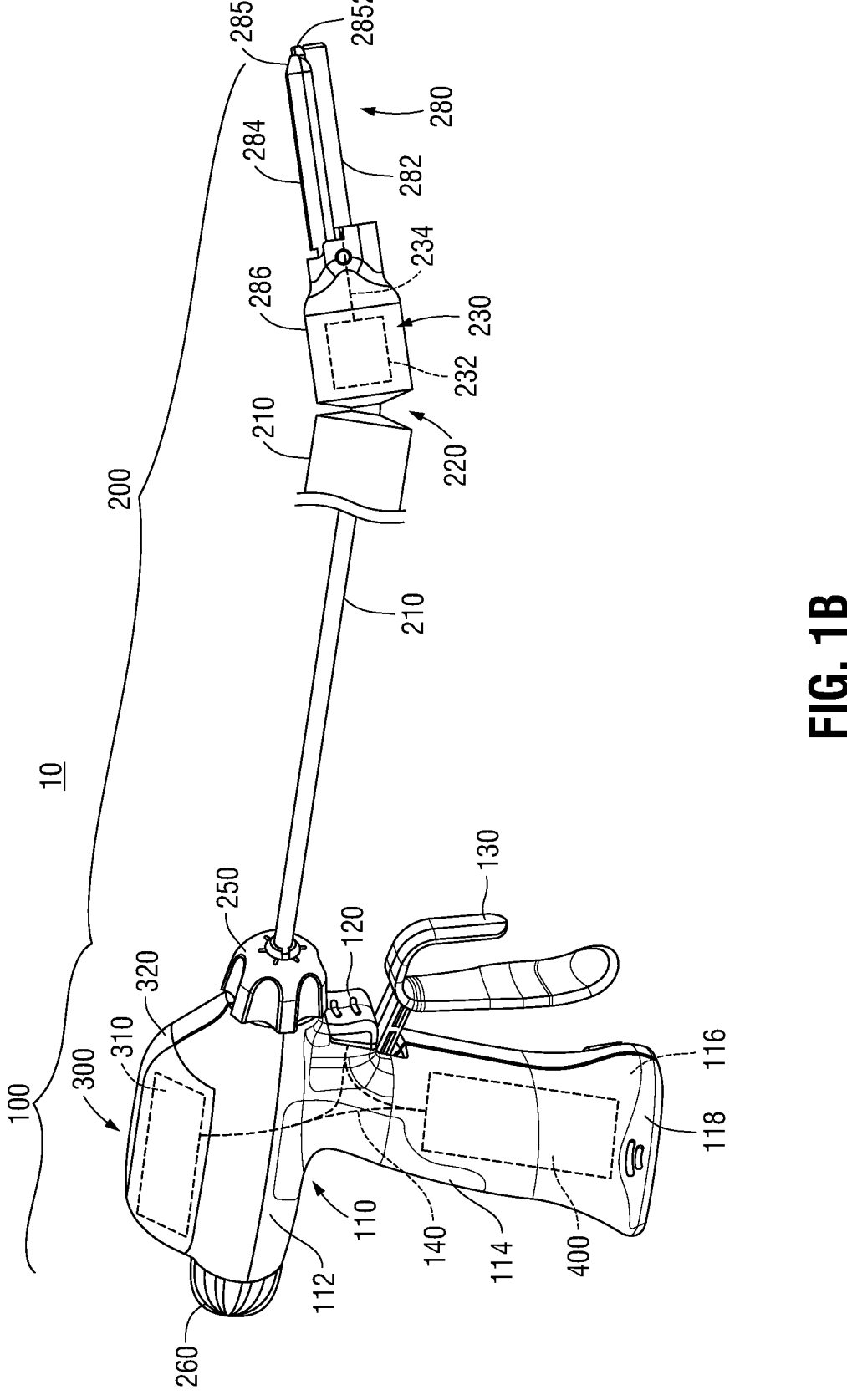
FIG. 1B is a perspective view of the hand-held articulating ultrasonic surgical instrument of FIG. 1A, disposed in an articulated position.

Referring generally to FIGS. 1A and 1B, an illustrative hand-held ultrasonic surgical instrument exemplifying the aspects and features of the present disclosure is shown generally identified by reference numeral 10. For the purposes herein, hand-held ultrasonic surgical instrument 10 is generally described. Aspects and features of hand-held ultrasonic surgical instrument 10 not germane to the understanding of the present disclosure are omitted to avoid obscuring the aspects and features of the present disclosure in unnecessary detail.

Hand-held ultrasonic surgical instrument 10 generally includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support a generator assembly 300 including generator electronics 310 disposed within an outer housing 320. Generator assembly 300 may be permanently engaged with body portion 112 of housing 110 or removable therefrom. Alternatively, generator assembly 300 may be remotely disposed and coupled to ultrasonic surgical instrument 10 by way of a cable.

Fixed handle portion 114 of housing 110 defines a compartment 116 configured to receive a battery assembly 400 and a door 118 configured to enclose compartment 116. An electrical connection assembly (not shown) is disposed within housing 110 of handle assembly 100 and serves to electrically couple activation button 120, generator assembly 300, and battery assembly 400 with one another when generator assembly 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. In configurations where generator assembly 300 is remote from ultrasonic surgical instrument 10, battery assembly 400 and the configuration of fixed handle portion 114 for receiving battery assembly 400 need not be provided, as the remote generator assembly 300 may be powered by a standard wall outlet or other remote power source.

Elongated assembly 200 of ultrasonic surgical instrument 10 includes an elongated shaft 210 having one or more articulating portions 220, an ultrasonic transducer assembly 230, a drive assembly (not shown), an articulation assembly (not shown), a rotation knob 250, an articulation knob 260, and an end effector 280 including a blade 282, a jaw 284, and a distal housing 286.

Elongated shaft 210 extends distally from body portion 112 of housing 110. The one or more articulating portions 220 are disposed along at least a portion of elongated shaft 210. More specifically, an articulating portion 220 is shown in FIGS. 1A and 1B in the form of an articulating joint disposed at a distal end portion of elongated shaft 210 and coupled to distal housing 286 of end effector 280 such that articulation of articulating portion 220 relative to a longitudinal axis of elongated shaft 210 articulates end effector 280 relative to the longitudinal axis of elongated shaft 210. However, it is also contemplated that additional or alternative articulating portions may be disposed along some or all of elongated shaft 210 periodically, intermittently, or continuously (for a portion or the entirety of elongated shaft 210). Each articulating portion 220 may include one or more articulation joints, linkages, flexible portions, malleable portions, and/or other suitable articulating structures to enable articulation of end effector 280 relative to the longitudinal axis of elongated shaft 210 in at least one direction, e.g., pitch articulation and/or yaw articulation. In configurations, the one or more articulating portions 220 are configured to enable both pitch articulation and yaw articulation; in other configurations, unlimited articulation in any direction is enabled.

Figure 3A:
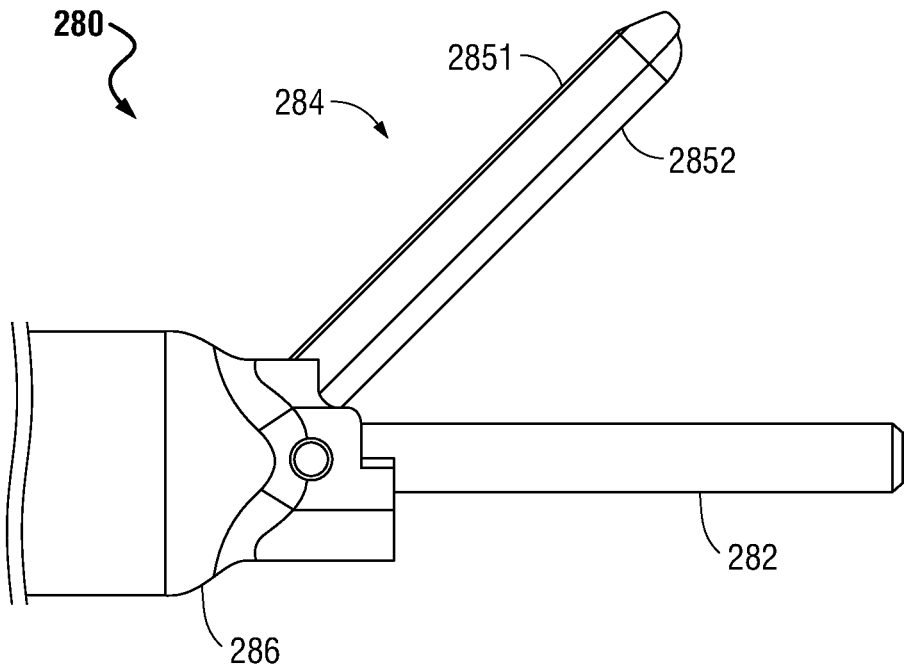
FIG. 3A is a side view of an end effector configured for use with the articulating ultrasonic surgical instrument of FIG. 1A, the robotic surgical system of FIG. 2, or any other suitable instrument or system, wherein a jaw thereof is disposed in an open position in a first orientation relative to a blade thereof.
Figure 3B:
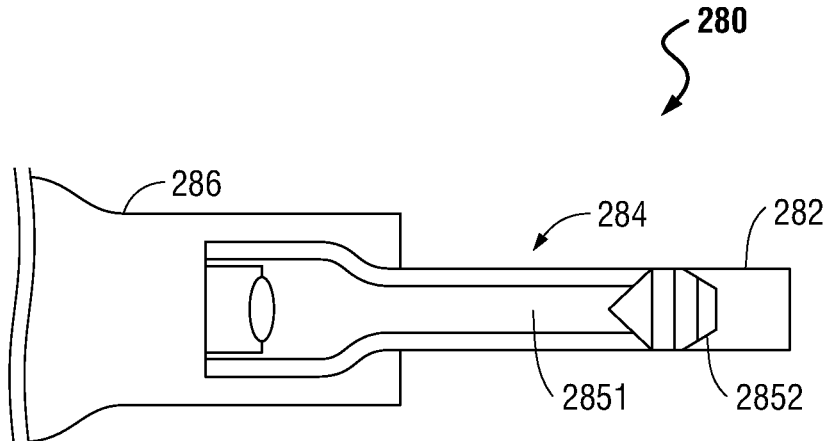
FIG. 3B is a side view of the end effector of FIG. 3A, wherein the jaw is disposed in the open position in a second orientation relative to the blade.

With additional reference to FIGS. 3A and 3B, jaw 284 is pivotably mounted on and extends distally from distal housing 286. The drive assembly operably couples clamp trigger 130 of handle assembly 100 with jaw 284 of end effector 280 by way of a jaw drive (not shown) such that clamp trigger 130 is selectively actuatable to pivot jaw 284 relative to distal housing 286 and blade 282 of end effector 280 from an open position to a clamping position for clamping tissue between jaw 284 and blade 282. The jaw drive may include one or more drive shafts, drive sleeves, drive cables, gears, cams, and/or other suitable components extending through or about handle assembly 100, elongated shaft 210 (including articulating portion 220 thereof), and distal housing 286 to operably couple clamp trigger 130 with jaw 284 to enable pivoting of jaw 284 between the open and clamping positions regardless of the articulation of articulating portion 220. Jaw 284, described in greater detail below, includes a more-rigid structural body 2851, which is pivotably mounted on a distal end portion of distal housing 286, and a more-compliant jaw liner 2852, which is captured by the more-rigid structural body 2851 and positioned to oppose blade 282 to enable clamping of tissue therebetween.

Rotation knob 250 is rotatable in either direction to rotate at least a portion of elongated assembly 200, e.g., at least distal housing 286 and jaw 284, in either direction relative to and about blade 282. More specifically, rotation knob 250 is operably coupled, by way of a rotation drive (not shown), to distal housing 286 and jaw 284 (and, in some configurations, other portions of elongated assembly 200 such as elongated shaft 210 or portions thereof), such that rotation of rotation knob 250 rotates distal housing 286 and jaw 284 about blade 282 to enable orientation of jaw 284 in any suitable radial orientation about blade 282, e.g., a first orientation shown in FIG. 3A or a second orientation shown in FIG. 3B. Thus, jaw 284 is capable of being pivoted relative to blade 282 between the open and clamping positions to clamp tissue between jaw 284 and blade 282 at any suitable radial orientation about blade 282 to, for example, enable treatment, e.g., sealing and/or cutting, of the clamped tissue at any suitable radial orientation. The rotation drive may include one or more drive shafts, drive sleeves, drive cables, gears, cams, and/or other suitable components extending through or about handle assembly 100, elongated shaft 210 (including articulating portion 220 thereof), to distal housing 286 and/or jaw 284 to operably couple rotation knob 250 with distal housing 286 and/or jaw 284 to enable rotation of jaw 284 about blade 282.

The articulation assembly may include gears, pulleys, sleeves, cables, etc. that operably couple articulation knob 260 with articulating portion 220 such that rotation of articulation knob 260 manipulates articulating portion 220 to thereby articulate end effector 280 relative to the longitudinal axis of elongated shaft 210. Alternatively, articulation knob 260 may be operably coupled to end effector 280 to induce the above-described articulating motion. Additional rotation and/or articulation actuators, assemblies, etc. and/or other suitable rotation and/or articulation actuators, assemblies, etc., manual or powered, are also contemplated such as, for example, to enable three degrees of freedom, e.g., rotation of distal housing 286 and jaw 284 about blade 282, rotation of elongated assembly 200 relative to handle assembly 100, and articulation of end effector 280 relative to the longitudinal axis of elongated shaft 210.

Referring back to FIGS. 1A and 1B, ultrasonic transducer assembly 230 includes an ultrasonic transducer 232 disposed within distal housing 286 and positioned distally of articulating portion 220, an ultrasonic horn 234 extending distally from ultrasonic transducer 232, and blade 282 which serves as the ultrasonic blade of end effector 280 extending distally from ultrasonic horn 234. Distal housing 286 and jaw 284 are rotatable about and relative to ultrasonic transducer assembly 230, as detailed above. As an alternative to positioning ultrasonic transducer 232 within distal housing 286 distally of articulating portion 220, ultrasonic transducer 232 and ultrasonic horn 234 may be positioned proximally of articulating portion 220, e.g., within a proximal portion of elongated shaft 210 or within housing 110. In configurations wherein ultrasonic transducer 232 and ultrasonic horn 234 are positioned proximally of articulating portion 220, a waveguide (not shown) including one or more articulating portions, e.g., flexible portions, joint portions, linkage portions, etc., is provided to extend through articulating portion 220 and interconnect ultrasonic horn 234 with blade 282 such that ultrasonic energy produced by ultrasonic transducer 232 is transmitted along the waveguide to blade 282, e.g., to treat (cut, seal, etc.) tissue, regardless of the articulation of articulating portion 220.

In some configurations, distal housing 286, including ultrasonic transducer 232 therein, defines an outer diameter less than about 15 mm, less than about 12 mm, less than about 10 mm, less than about 8 mm, less than about 5 mm, or less than about 3 mm, wherein "about" and similar terms as utilized herein account for material, manufacturing, use, measurement, environment, etc. tolerances and may encompass differences of up to 10%. As such, ultrasonic transducer 232, in such configurations, may define a sufficiently small diameter so as to enable operable receipt within distal housing 286 of the above-noted dimensions, respectively. By providing a configuration with the above-noted outer diameters, ultrasonic surgical instrument 10 may be utilized minimally-invasively through standard sizes of access devices.

Ultrasonic transducer 232 may include a stack of piezoelectric elements secured, under pre-compression between proximal and distal end masses or a proximal end mass and ultrasonic horn 234 with first and second electrodes electrically coupled between piezoelectric elements of the stack of piezoelectric elements to enable energization thereof to produce ultrasonic energy. However, other suitable ultrasonic transducer configurations, including plural transducers and/or non-linear transducers are also contemplated. Electrical lead wires (not shown) connect the electrodes of ultrasonic transducer 232 with generator assembly 300 to enable an electrical drive signal generated by generator assembly 300 to be imparted to the stack of piezoelectric elements of ultrasonic transducer 232 to energize the stack of piezoelectric elements to produce ultrasonic energy for transmission to blade 282 via ultrasonic horn 234 for treating tissue.

Ultrasonic horn 234 is engaged to the stack of piezoelectric elements of ultrasonic transducer 232 and extends distally therefrom. Blade 282 is unitarily formed with or engaged with ultrasonic horn 234 and extends distally therefrom.

With additional reference, once again, to FIGS. 3A and 3B, blade 282, as described in greater detail below, defines a substantially straight, substantially cylindrical configuration. This configuration enables clamping of tissue between blade 282 and jaw 284 at any rotational orientation of jaw 284 relative to blade 282, e.g., the first orientation illustrated in FIG. 3A or the second orientation illustrated in FIG. 3B. Blade 282 may alternatively define other suitable cross-sectional configurations, e.g., polygonal configurations or other suitable radially-symmetric configurations, and/or may include tapers along the length thereof, while still enabling rotation of jaw 284 about and clamping jaw 284 with blade 282 at a plurality of orientations relative to blade 282.

Figure 2:
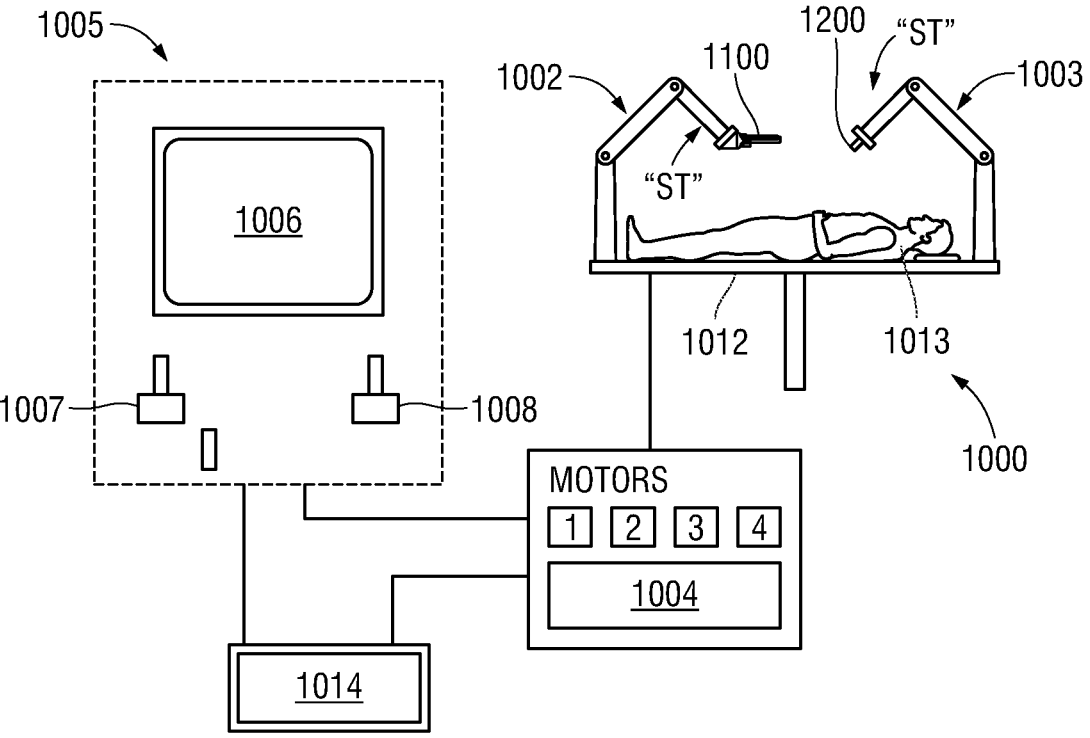
FIG. 2 is a schematic illustration of a robotic surgical system configured for use with an articulating ultrasonic surgical instrument, provided in accordance with the present disclosure.

Referring generally to FIG. 2, an illustrative robotic surgical system exemplifying the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003. Robotic surgical system 1000 may be configured for use on a patient 1013 lying on a patient table 1012 to be treated in a minimally invasive or other suitable manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, to which may be attached, for example, a surgical tool "ST" supporting an end effector 1100, 1200. End effector 1100 may be configured as an articulating ultrasonic surgical instrument similarly as detailed above with respect to instrument 10 (FIGS. 1A and 1B) except that housing 110 of handle assembly 100 (FIGS. 1A and 1B) is configured to connect to robot arm 1002 and any manual controls or features of instrument 10 (FIGS. 1A and 1B) are modified appropriately such that manipulation, actuation, and the other functions of instrument 10 (FIGS. 1A and 1B) are effected by robot arm 1002 rather than manually by a user. End effector 1200 may be any other suitable surgical end effector, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, and, thus, the surgical tools "ST" (including end effectors 1100, 1200) execute a desired movement and/or function according to a corresponding input from manual input devices 1007, 1008, respectively. Control device 1004 may also be configured in such a way that it regulates the movement of robot arms 1002, 1003 and/or of the motors.

Figures 4A, 4B, 4C:
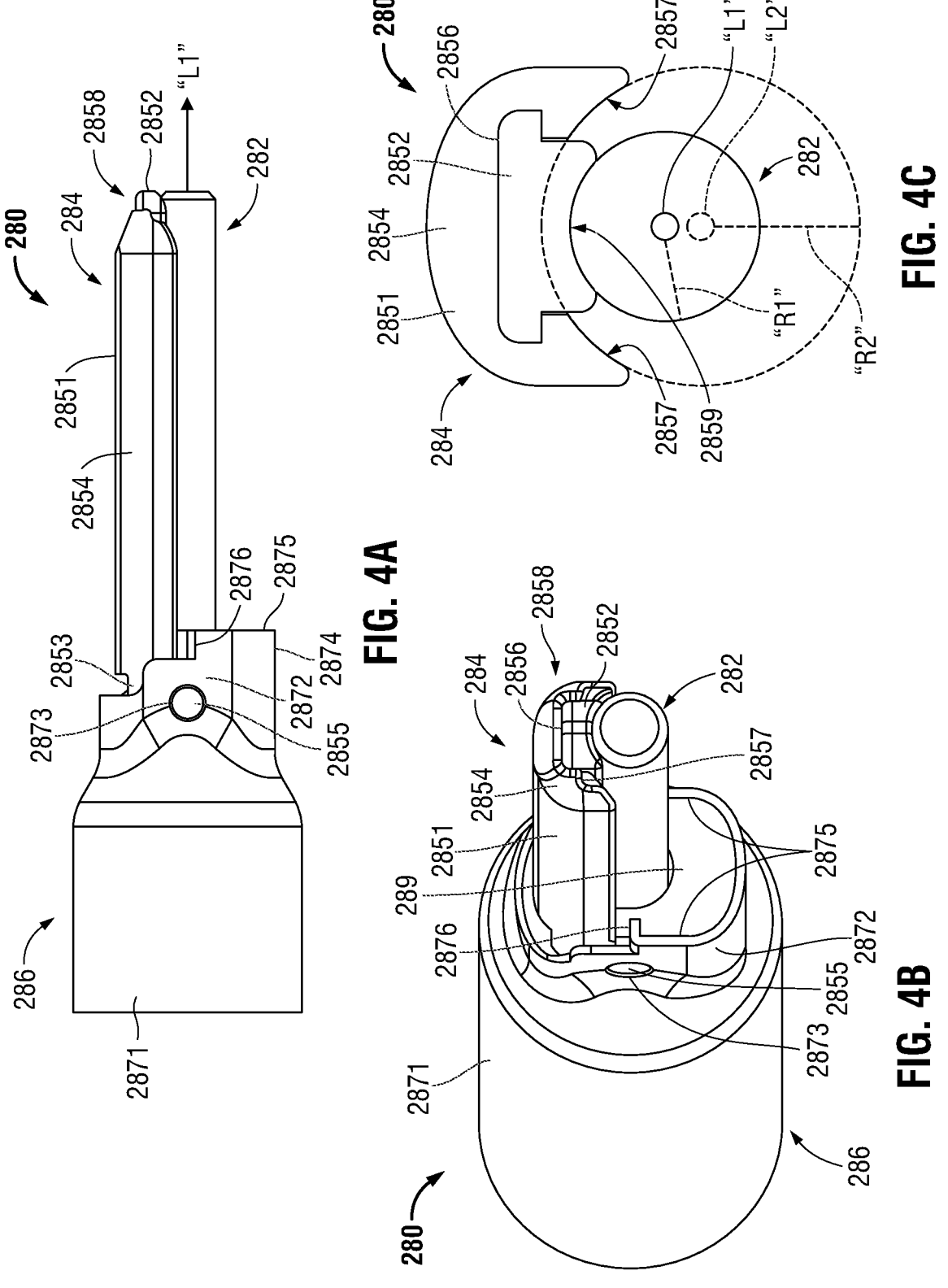
FIGS. 4A-4C are side, front perspective, and transverse cross-sectional views, respectively, of the end effector of FIG. 3A, wherein the jaw is disposed in the clamping position in the first orientation relative to the blade.

Turning to FIGS. 4A-4C, end effector 280 is described in greater detail. As noted above, end effector 280 includes blade 282, jaw 284, and distal housing 286. Blade 282 has a substantially straight, substantially cylindrical configuration and, thus, defines a central longitudinal axis "L1" and a radius "R1" extending perpendicularly from the central longitudinal axis "L1" to the outer annular surface of blade 282. For the purposes herein, "substantially cylindrical" includes not fully cylindrical blades such as, for example, a blade that includes one or more non-cylindrical features that occupy less than about 10% of the outer annular periphery of the blade and/or extend less than about 10% of an operative length of the blade, higher-order polygonal configurations that generally approximate a cylinder, e.g., an octagon, decagon, dodecagon, etc., and other suitable cylindrical-approximating configurations.

Jaw 284, as also noted above, includes more-rigid structural body 2851 and more-compliant jaw liner 2852. Structural body 2851 may be formed from a metal, e.g., stainless steel, and includes a proximal flange portion 2853 and an elongated distal portion 2854. Proximal flange portion 2853 of structural body 2851 is disposed within distal neck 2872 of distal housing 286 and defines a bifurcated configuration to enable passage of blade 282 therebetween. Proximal flange portion 2853 includes a pivot boss 2855 extending outwardly from each side thereof. Pivot bosses 2855 are received within opposed apertures 2873 defined within distal neck 2872 of distal housing 286 to pivotably couple jaw 284 to distal housing 286. Further, the jaw drive (not shown) may be coupled to proximal flange portion 2853 at a position offset from pivot bosses 2855 such that sliding of at least a distal portion of the jaw drive urges jaw 284 to pivot about pivot bosses 2855 and relative to distal housing 286 and blade 282 between the open and clamping positions.

Elongated distal portion 2854 of structural body 2851 of jaw 284 includes a longitudinal channel 2856 defined within a blade-facing surface 2857 of elongated distal portion 2854 and extending along at least a portion of a length thereof. Longitudinal channel 2856 may define a T-shaped, L-shaped, or other suitable keyed configuration to facilitate slidable engagement and retention of more-compliant jaw liner 2852 therein. Elongated distal portion 2854 further includes a distal end portion 2858 having a chamfered outwardly-facing or top surface and under-cut inwardly-facing or lower surfaces disposed on either side of morecomplaint jaw liner 2852. This configuration facilitates blunt dissection using end effector 280. Additionally or alternatively, a distal end portion of jaw liner 2852 may be similarly chamfered to facilitate blunt dissection.

Blade-facing surface 2857 of elongated distal portion 2854 of structural body 2851 of jaw 284 extends on either side of longitudinal channel 2856 (being interrupted thereby) and has an arcuate configuration defining a continuous radius of curvature "R2" defined from a central longitudinal axis "L2" (of an imaginary cylinder that conforms to blade-facing surface 2857) to blade-facing surface 2857. Central longitudinal axis "L1" of blade 282 and central longitudinal axis "L2" associated with blade-facing surface 2857 of elongated distal portion 2854 of structural body 2851 of jaw 284 are substantially parallel with one another but offset from one another when jaw 284 is disposed in the clamping position. That is, in the clamping position of jaw 284, a vertical line bisecting a transverse cross-section of blade 282 and jaw 284, e.g., a transverse cross-section as shown in FIG. 4C, intersects both axes "L1" and "L2," but a horizontal line bisecting a transverse cross-section of blade 282, e.g., a transverse cross-section as shown in FIG. 4C, intersects axis "L1" but does not intersect axis "L2." Indeed, a horizontal line intersecting axis "L2" is disposed in parallel orientation relative to a horizontal line intersecting axis "L1." Axis "L2" may be offset below, e.g., in a direction opposite jaw 284 from, axis "L1." In this manner, in the clamping position of jaw 284, a radial distance (relative to axis "L1") from the outer surface of blade 282 to blade-facing surface 2857 is smaller towards the inner sides of blade-facing surface 2857, e.g., on either side of longitudinal channel 2856, as compared to the radial distance from the outer surface of blade 282 to blade-facing surface 2857 towards the outer side edges of blade-facing surface 2857.

Jaw liner 2852 defines a complementary configuration to longitudinal channel 2856, e.g., a T-shaped, L-shaped, or other suitable keyed configuration, to facilitate slidable engagement and retention of jaw liner 2852 within longitudinal channel 2856. Jaw liner 2852 may be formed from PTFE or other suitable resilient material to facilitate clamping tissue between jaw liner 2852 and blade 282 and to inhibit damage to blade 282 and/or structural body 2851 by being capable of absorbing some of the ultrasonic vibration energy from blade 282 when disposed in contact (direct or indirect) therewith.

Jaw liner 2852 may define an arcuate blade-facing surface 2859 (notwithstanding texture such as gripping teeth or recesses defined therein) defining a third radius of curvature that is substantially equal to radius "R1" of blade 282, although non-arcuate, e.g., planar, multi-angle, multi-curve, etc., surfaces and/or an arcuate surface with a different radius from radius "R1" are also contemplated. With respect to configurations where the arcuate blade-facing surface 2859 defines a third radius of curvature that is substantially equal to radius "R1" of blade 282 (as well as in other suitable configurations), gripping tissue between jaw liner 2852 and blade 282 is facilitated, consistent sealing and cutting capabilities are achieved, and longevity of jaw liner 2852 is increased in that any wear thereon is evenly or more-evenly distributed across jaw liner 2852. The third radius of curvature is centered on a longitudinal axis that may be coaxial with or parallel to the longitudinal axis "L1" of blade 282, although offset configurations are also contemplated.

Blade-facing surface 2857 of elongated distal portion 2854 of structural body 2851 of jaw 284 is recessed relative to blade-facing surface 2859 of jaw liner 2852 within the width of blade 282; however, outside the width of blade 282, blade-facing surface 2857 may extend beyond jaw liner 2852 towards blade 282. This, in combination with the offset axes "L1" and "L2" of blade 282 and blade-facing surface 2857, respectively, provides a varied clamping profile transversely across blade 282 when jaw 284 is disposed in the clamping position clamping tissue between jaw 284 and blade 282, which increases tissue gripping capability while allowing for release of tissue after treatment, e.g., sealing and cutting, with little or no opening of jaw 284 required. In other configurations, blade-facing surface 2857 is contained within or extends the width of blade 282 and/or does not extend beyond jaw liner 2852 towards blade 282.

Referring still to FIGS. 4A-4C, distal housing 286 includes a proximal body 2871 and a distal neck 2872 extending distally from proximal body 2871. Proximal body 2871 houses ultrasonic transducer 232 therein and, in some configurations, is rotatable relative to ultrasonic transducer 232, e.g., to enable rotation of distal housing 286 and jaw 284 relative to ultrasonic transducer 232 and blade 282. Distal neck 2872 defines a reduced height and/or width dimension as compared to proximal body 2871. Further, distal neck 2872 includes a U-shaped extension portion 2874 that extends distally to overlap relatively small lengths of the operable portion of blade 282 (defined as the portion of blade 282 against which jaw liner 2852 is capable of clamping tissue), elongated distal portion 2854 of structural body 2851, and/or jaw liner 2852 (for example, overlapping less than about 20% of the length of one or more thereof). The uprights 2875 of U-shaped extension portion 2874 are disposed on either side of blade 282 and extend towards jaw 284 to shelves 2876 defined at the free ends of uprights 2875 and disposed substantially perpendicularly relative thereto. With U-shaped extension portion 2874 extending to overlap the relatively small lengths, the underside of blade 282 remains substantially exposed to, for example, facilitate the use thereof for enterotomies, backscoring, and/or other surgical tasks.

Shelves 2876 oppose the outer side edges of elongated distal portion 2854 of structural body 2851 of jaw 284 in the clamping position of jaw 284. However, shelves 2876 are recessed relative to blade 282 in that blade 282 extends farther towards jaw 284 as compared to shelves 2876. As manufactured and during typical use, jaw liner 2852 maintains a gap between the outer side edges of elongated distal portion 2854 of structural body 2851 of jaw 284 and shelves 2876 even after typical wear of jaw liner 2852. However, over prolonged use or in certain instances, jaw liner 2852 may wear more significantly such that the outer side edges of elongated distal portion 2854 contact shelves 2876 in the clamping position of jaw 284. In such instances, shelves 2876 serve as jaw stops to inhibit further wear (e.g., complete wear-through) of jaw liner 2852, thus preventing damage and/or injury.

A plug 289 is seated within distal neck 2872 of distal housing 286, substantially filling (together with the other components extending through distal neck 2872) an interior cross-sectional area of distal neck 2872. Plug 289 surrounds at least a portion of blade 282 without inhibiting the ultrasonic motion thereof. Plug 289 may be formed from any suitable material such as, for example a compliant material, e.g., PTFE, silicone, etc., or other suitable material, and serves to inhibit contact between blade 282 and distal neck 2872 and/or other components extending through distal neck 2872. Plug 289 further substantially inhibits the passage of tissue, eschar, and/or other debris proximally into distal housing 286. In aspects, plug 289 may be omitted.

Figures 5A, 5B, 5C:
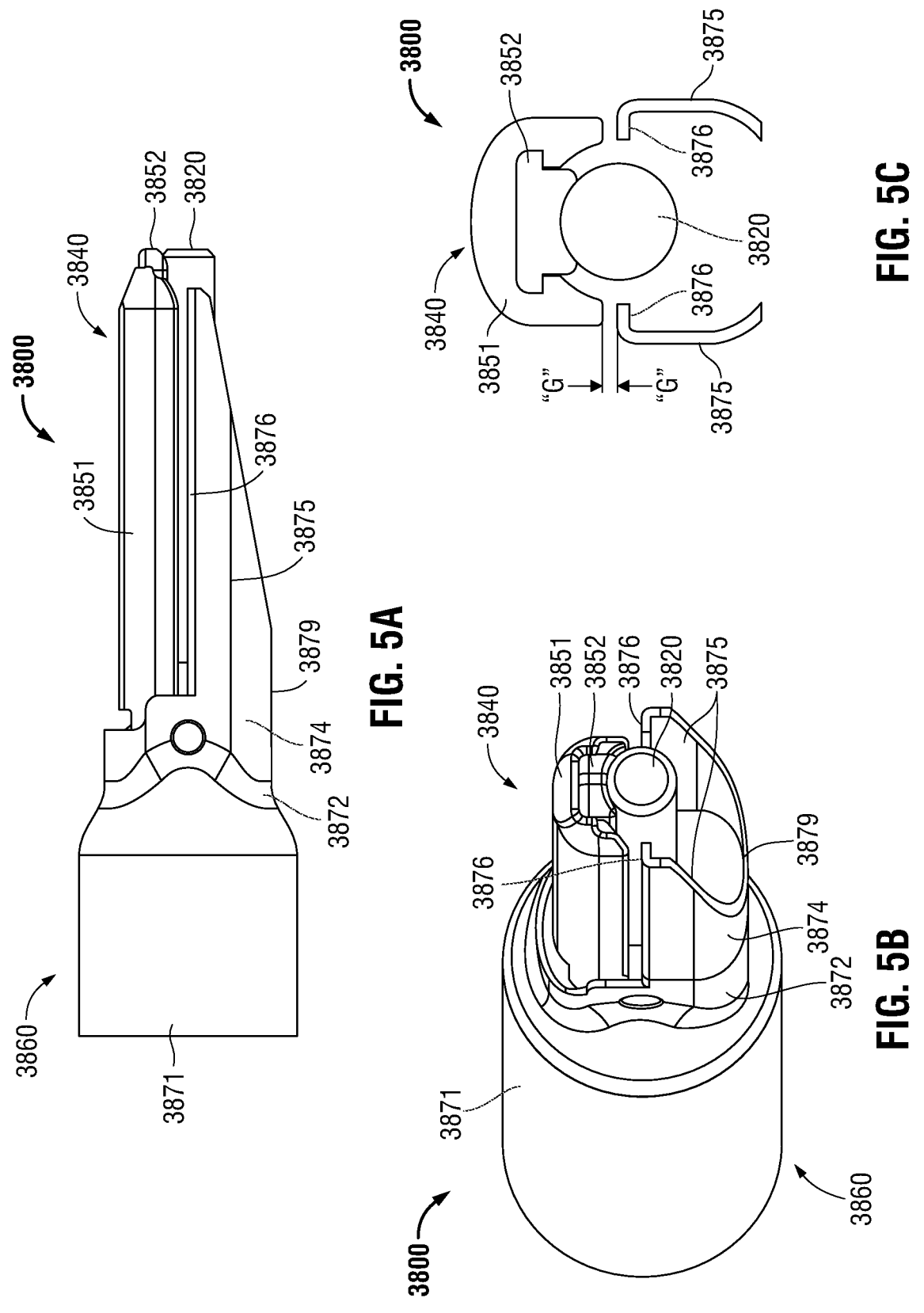
FIGS. 5A-5C are side, front perspective, and transverse cross-sectional views, respectively, of another end effector configured for use with the articulating ultrasonic surgical instrument of FIG. 1A, the robotic surgical system of FIG. 2, or any other suitable instrument or system, wherein a jaw thereof is disposed in a clamping position.

Turning to FIGS. 5A-5C, another end effector 3800 configured for use in accordance with the present disclosure with any of the instruments or systems detailed herein or any other suitable instruments or systems is shown. End effector 3800 is similar to and may include any of the features of end effector 280 (FIGS. 4A-4C). Accordingly, only differences between end effector 3800 and end effector 280 (FIGS. 4A-4C) are described in detail below for purposes of brevity, while similarities are summarily described or omitted entirely.

End effector 3800 includes a blade 3820, a jaw 3840, and distal housing 3860. Jaw 3840 includes a more-rigid structural body 3851 and more-compliant jaw liner 3852. Distal housing 3860 includes a proximal body 3871 and a distal neck 3872 extending distally from proximal body 3871. Distal neck 3872 includes an extension portion 3874 that extends distally to overlap relatively large lengths of the operable portion of blade 3820, elongated distal portion 3854 of structural body 3851, and/or jaw liner 3852 (for example, overlapping more than about 80% of the length of one or more thereof). Extension portion 3874 defines uprights 3875 that are disposed on either side of blade 3820 and extend towards jaw 3840 to shelves 3876 defined at the free ends of uprights 3875. Uprights 3875 extend the relatively large lengths of the operable portion of blade 3820, elongated distal portion 3854 of structural body 3851, and/or jaw liner 3852.

Extension portion 3874 defines a U-shaped proximal base wherein uprights 3875 are connected by a backspan 3879 extending across an underside of blade 3820. Backspan 3879 extends to overlap only relatively small lengths of the operable portion of blade 3820, elongated distal portion 3854 of structural body 3851, and/or jaw liner 3852 (for example, overlapping less than about 20% of the length of one or more thereof). Uprights 3875 taper in height, from the lower ends thereof and in a proximal-to-distal direction, from backspan 3879 to the free distal ends of uprights 3875. As a result, shelves 3876 are maintained in position relative to blade 3820 along the lengths of shelves 3876, while the bottom portion and lateral sides of blade 3820 are increasing exposed in a proximal-to-distal direction due to the tapering height of uprights 3875 from the lower ends thereof. This configuration facilitates use of the distal, bottom portion of blade 3820, e.g., for enterotomies, backscoring, and/or or other surgical tasks.

In some configurations, extension portion 3874 may be adapted to connect to a source of Radio Frequency (RF), energy or other suitable energy, to provide tissue interrogation and/or tissue treatment in conjunction with blade 3820 and/or structural body 3851 of jaw 3840 (or other isolated electrically-conductive surfaces disposed on structural body 3851 of jaw 3840). End effector 280 (FIGS. 4A-4C) may likewise be configured in a similar manner.

More specifically, to supply RF energy for interrogating tissue, for example, an interrogation signal may be transmitted to blade 3820 and/or structural body 3851 of jaw 3840 via a first electrical path, e.g., an RF signal at a positive potential (+), and a second, different potential may be established at extension portion 3874, e.g., a negative potential (–), such that the interrogation signal is transmitted from blade 3820 and/or structural body 3851 of jaw 3840 through tissue, to uprights 3875 of extension portion 3874 due to the potential difference therebetween and returned via a second, different electrical path, thus allowing evaluation of the returned signal.

With respect to the supply of RF energy for treating tissue, blade 3820 and/or structural body 3851 of jaw 3840 are energized to a first potential via a first electrical path, e.g., RF energy at a positive potential (+), and extension portion 3874 is energized to a second, different potential via a second, different electrical path, e.g., RF energy at a negative potential (–), to enable the conduction of bipolar RF tissue-treating current from blade 3820 and/or structural body 3851 of jaw 3840 through tissue, to uprights 3875 of extension portion 3874, to treat, e.g., seal and/or cut, the tissue disposed therebetween, either in conjunction with the application of ultrasonic energy to the tissue or separately therefrom.

A gap "G" is maintained between the outer side edges of elongated distal portion 3854 of structural body 3851 of jaw 3840 and shelves 3876 of uprights 3875 such that, in configurations structural body 3851 and shelves 3876 are energized to different potentials, shorting is inhibited; further, end effector 3800 is configured such that the gap "G" is appropriate for RF-based tissue interrogation and/or treatment.

It should be understood that various aspects disclosed herein may be combined in different combinations than the combinations specifically presented in the description and accompanying drawings. Further, while several embodiments of the disclosure are presented in the description and accompanying drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector of an ultrasonic surgical instrument, comprising:

an ultrasonic blade having a substantially cylindrical configuration; and a jaw including a structural body and a jaw liner engaged with the structural body and positioned such that a blade-facing surface of the jaw liner is disposed between first and second blade-facing surfaces of the structural body, the first and second blade-facing surfaces of the structural body being tissue-contacting surfaces, the jaw movable relative to the ultrasonic blade from an open position to a clamping position, wherein, in the clamping position, the blade-facing surface of the jaw liner opposes the ultrasonic blade with the first and second blade-facing surfaces of the structural body disposed on either side of the blade-facing surface of the jaw liner and the ultrasonic blade, wherein the ultrasonic blade defines a first longitudinal axis and a first radius, the first and second blade-facing surfaces of the structural body cooperate to define a second radius centered on a second longitudinal axis, and the blade-facing surface of the jaw liner defines a third radius centered on a third longitudinal axis, and wherein the first radius and the second radius are different from one another and the blade-facing surface of the jaw liner protrudes towards the ultrasonic blade beyond at least a portion of the first blade-facing surface of the structural body and the second blade-facing surface of the structural body.

2. The end effector according to claim 1, wherein the first and second longitudinal axes are substantially parallel and offset relative to one another in the clamping position of the jaw.

3. The end effector according to claim 2, wherein the first longitudinal axis is vertically offset farther towards the jaw as compared to the second longitudinal axis in the clamping position of the jaw.

4. The end effector according to claim 1, wherein the first radius and the third radius are substantially equal and wherein the first and third longitudinal axes are substantially coaxial with one another.

5. The end effector according to claim 1, wherein, in the clamping position of the jaw, at least a portion of each of the first and second blade-facing surfaces of the structural body protrudes beyond the blade-facing surface of the jaw liner.

6. The end effector according to claim 1, wherein the jaw is rotatable about the ultrasonic blade to a plurality of different orientations, and wherein the jaw is movable to the clamped position in each of the plurality of different orientations to oppose the blade-facing surface of the jaw liner with a plurality of different surface portions of the ultrasonic blade.

7. The end effector according to claim 1, further comprising a distal housing, wherein the structural body of the jaw is pivotably coupled to the distal housing and wherein the ultrasonic blade extends distally from the distal housing.

8. The end effector according to claim 7, further comprising a plug disposed within the distal housing and surrounding the ultrasonic blade, the plug configured to inhibit passage of material proximally into the distal housing.

9. The end effector according to claim 7, further comprising an ultrasonic transducer disposed within the distal housing and operably coupled to the ultrasonic blade.

*   *   *   *   *